United States Patent [19]

Murray

[11] Patent Number: 4,778,834

[45] Date of Patent: Oct. 18, 1988

[54] HYDROXYLAPATITE-SYNTHETIC RESIN COMPOSITES

[75] Inventor: Douglas G. Murray, North York, Canada

[73] Assignee: Sterling Drug Inc., New York, N.Y.

[21] Appl. No.: 18,367

[22] Filed: Feb. 24, 1987

[51] Int. Cl.⁴ .............................................. C08K 9/06
[52] U.S. Cl. ................................... 523/212; 523/210; 524/560; 524/706; 524/789; 524/790
[58] Field of Search ................ 523/210, 212; 524/560, 524/706, 789, 790

[56] References Cited

U.S. PATENT DOCUMENTS

| | | | |
|---|---|---|---|
| 3,423,828 | 1/1969 | Halpern et al. | 32/8 |
| 3,423,829 | 1/1969 | Halpern et al. | 32/8 |
| 3,423,830 | 1/1969 | Halpern et al. | 318/148 |
| 4,097,935 | 7/1978 | Jarcho | 3/1.9 |
| 4,281,991 | 8/1981 | Michl et al. | 433/202 |
| 4,364,731 | 12/1982 | Norling et al. | 433/218 |
| 4,373,217 | 2/1983 | Draenert | 3/1.9 |
| 4,378,248 | 3/1983 | Griffith | 106/35 |
| 4,381,918 | 5/1983 | Ehrnford | 433/109 |
| 4,411,625 | 10/1983 | Koblitz et al. | 433/217 |
| 4,427,799 | 1/1984 | Orlowski et al. | 523/116 |
| 4,431,421 | 2/1984 | Kawahara et al. | 433/228 |
| 4,433,958 | 2/1984 | Fellman et al. | 433/199 |
| 4,451,235 | 5/1984 | Okuda et al. | 433/201 |
| 4,491,453 | 1/1985 | Koblitz et al. | 433/217 |

*Primary Examiner*—Melvyn I. Marquis
*Attorney, Agent, or Firm*—William G. Webb; Paul E. Dupont

[57] ABSTRACT

Composites useful, for example, in dental restorative procedures comprising a mixture of particulate ceramic hydroxylapatite and a polymerizable monomer or mixture of polymerizable monomers wherein said ceramic hydroxylapatite particles, prior to mixing and polymerizing with said polymerizable monomers, are coated first with a siliceous material and then with an organosilane and a process for preparation of the same.

24 Claims, No Drawings

HYDROXYLAPATITE-SYNTHETIC RESIN COMPOSITES

BACKGROUND OF THE INVENTION

This invention relates to hydroxylapatite-synthetic resin composites useful, for example, in dental restorative procedures and to a process for the preparation of the same.

INFORMATION DISCLOSURE STATEMENT

In view of the long term toxic effects of mercury, the use of silver-mercury amalgams, once highly favored in the dental profession in dental restorative processes such as in the filling of teeth, has in recent years fallen into disfavor, and substitutes for silver-mercury amalgams, which retain their excellent strength and water stability properties but which lack the undesired toxic properties, are being sought.

While some use has been made of plastic materials for dental restorative use, these materials alone generally lack the necessary strength characteristics.

An ideal dental restorative material would be one which has the general properties of teeth, and in the search for such ideal dental restorative materials, much attention has been focused on a variety of inorganic materials such as the calcium phosphates which have many of the physical as well as the chemical properties of teeth.

In view of the general similarity of hydroxylapatite to the mineral phase of teeth, the use of hydroxylapatite in combination with other materials, such as synthetic plastics, as a composite dental restorative appears to offer the greatest potential promise.

Ideally such composites must not only possess sufficient strength to function properly as dental restorative materials, they must, in addition, and more importantly, be resistant to any hydrolytic action between the components making up the composite so that the strength inherent in the dry composite is not diminished to the point of impairment in the moist environment of the mouth. However, to the extent that the prior art addresses the question of the water resistance of plastic-containing dental composites, it has approached the problem by determining the degree of water absorption by dental composites without relating the absorption to the principal problem which is whether, and to what degree, such water absorption affects the strength of the composites. The heart of the problem thus remains unresolved.

Thus U.S. Pat. Nos. 3,423,828, 3,423,829 and 3,423,830 disclose artificial teeth composed of dental porcelain particles and a synthetic dental plastic bonded together by an organic silicon bonding agent. The teeth are prepared by coating the porcelain particles, such as feldspathic, nepheline syenite and synthetic porcelains, such as alumina-base porcelains, with an organosilane and then mixing the coated particles with a polymeric agent, such as polymethacrylates, and polymerizing the mixture. In one embodiment disclosed in U.S. Pat. No. 3,423,829, the artificial teeth comprise an outer shell of porcelain and an inner core of either reinforcing strong porcelain, synthetic resin or a combination of synthetic resin and reinforcing strong porcelain, the various portions being bonded to one another through chemical union with an organic silicon compound.

U.S. Pat. No. 4,097,935 discloses a dental restorative composition comprising a blend of ceramic hydroxylapatite with a polymerized or polymerizable material, which may consist of a single monomer or a mixture of monomers with an appropriate polymerization catalyst, hardener, promoter, accelerator or cross-linking agent. Optionally an organosilane can be included as a keying agent to promote the bonding of the ceramic material to the resin and of the composite to the tooth.

U.S. Pat. No. 4,281,991 discloses materials for dental purposes, such as tooth fillings, cements, sealing and protective coatings, crown and bridge materials or prosthetic devices, comprising a microfine inorganic filler, such as the oxides of aluminum and silicon, silicate glasses or calcium carbonate, but preferably silica or alumina, silanized with an organosilane, for example, $\gamma$-methacryloxypropyltrimethoxysilane. The silanized particulate filler is then admixed with a two component polymeric material such as the bis-glycidyl methacrylate adduct of bis phenol A, 2,2-bis-[4-(2-hydroxypropoxy)phenyl]propane (hereinafter bis-GMA), and "difunctional esters of acrylic or methacrylic acid", for example ethylene glycol methacrylate. The patentee states that the water absorption of the composite material at the end of two months is between 0.5 and 1.5% and describes the assertedly superior properties of the compositions in terms of compressive strength, good polishability, excellent transparency, with low abrasion, and good opalescence, which gives the material the appearance of natural teeth.

U.S. Pat. No. 4,364,731 discloses a method of bonding polymeric materials to a substrate used, for example, for dental crowns via a silane coupling agent, the substrate having been coated with an inorganic oxide. A preferred substrate is stainless steel. Suitable inorganic oxides are alumina, silica, aluminate, silicate, aluminosilicate compounds and silica-rich glasses, silica being preferred. A variety of organosilanes are said to be suitable, and a preferred coupling agent is said to be Z-6032, N-[(ethenylphenyl)methyl]-N'-[3-(trimethoxysilyl)propyl]-1,2-ethanediamine hydrochloride.

U.S. Pat. No. 4,373,217 discloses bone implant material composed of a mixture of a "special tricalcium phosphate" in a specific amount and in an exactly defined particle size and "conventional bone cements based on polyacrylates". The patentee specifically states that the calcium phosphate "is to be resorbed" on the surface of the implant, and that it is advantageous that the phosphate throughout the mass be rapidly resorbed into the body. He also emphasizes the necessity of preventing absorption of the liquid monomer into the pores of the phosphate so as to ensure its porosity and suggests one way of accomplishing that objective is to treat the solid phosphate with a physiologically compatible "filler", such as glycols.

U.S. Pat. No. 4,378,248 discloses a dental porcelain having incorporated therein a particulate ion-leachable glass capable of crosslinking with a polycarboxylate by leaching out the calcium ions.

U.S. Pat. No. 4,381,918 describes a method of making a composite of porous inorganic particles and a resin used as a dental material. The method involves compressing a mixture of the inorganic particles, which are partially or completely impregnated with an at least partially hardenable resin material, so that the particles contact each other, and pressure in the liquid resin causes flow of the resin into the pores of the particulate matter. The particles are bonded together by hardening of at least a portion of the hardenable resin thus producing a resin structure which has a contiguous inorganic phase with "mechanical interlocking" of the phases. An inorganic fibrous material, typically from fiber glass, is optionally mixed with the composition, and the patentee also discloses that, in order to further enhance adhesion between the inorganic constituent and the resin, the inorganic material can be pretreated with "an appropriate organo functional silane coupling agent". The inorganic particles are said to be preferably aluminum oxide or silicon dioxide, and the resins include, for example, methacrylates.

U.S. Pat. No. 4,411,625 discloses irradiation curable dental restoratives containing, as a major component, an inorganic filler, such as barium aluminum silicate; lithium aluminum silicate; strontium, lanthanum or tantalum glasses; silica; and quartz which can be optionally and preferably silanated. The compositions contain, as a minor component, a binder resin, diluent monomer and a photosensitizer system comprising an $\alpha$-diketone photosensitive species, an amine reducing agent and an ultraviolet photosensitizer selected from the family of benzoin alkyl ethers. A combination containing 60:40 microfine silanated silica:2–5 micron silanated barium aluminum silicate, dis-GMA, and triethylene glycol dimethacrylate (hereinafter TEGMA) is specifically disclosed in Example 3.

U.S. Pat. No. 4,427,799 discloses a dental restorative material containing silanized inorganic microfiller, a macrofiller, and a polymerizable component such as bisGMA.

U.S. Pat. No. 4,431,421 discloses compositions useful for medical or dental restorations comprising a silanated filler, such as powdered quartz, powdered glass, glass beads, powdered aluminum oxide, borosilicate glass, barium glass, hydroxyapatite, and aluminosilicate and a predominant amount of an acrylic monomer based on acrylate esters of dipentaerythritol, e.g. dipentaerythritol hexacrylate (DPE-6A) and dipentaerythritol hexamethacrylate (DPE-6M), which can be used in combination with other monomers, such as bis-GMA. The dipentaerythritol esters are said to offer good water resistance. The compressive strength, abrasion loss, bonding strength, water sorption, and discoloration of composites within the ambit of the invention prepared from dipentaerythritol esters were determined and compared with the properties of composites prepared from other acrylate esters, such as bis-GMA and TEGMA. No comparisons of the loss of strength after prolonged water exposure were made, however, between any of the test samples, and the water resistance of the compositions of the invention, as determined by the amount of water absorbed, was attributed to the nature of the dipentaerythritol esters used as monomers.

U.S. Pat. No. 4,433,958 discloses compositions for permanent dental restorations comprising (a) a liquid monomer system comprised of one or more monoethylenically unsaturated monomers and one or more polyethylenically unsaturated cross linking monomers of the mono- or polyfunctional acrylate or methacrylate class; (b) a mixture of an organic polymeric particulate substance insoluble in the liquid monomer system and an inorganic particulate substance; and (c) a free radical initiator system such as a redox system. The particulate organic and inorganic materials have a Moh hardness up to about 5 so as to produce dental restoratives that are not excessively abrasive. Typical inorganics with the necessary Moh hardness rating are said to be hydroxyapatite, stearate-coated calcium carbonate, calcium carbonate, calcium metasilicate, talc, clay, calcium sulfate, or combinations thereof. Others with a Moh rating in excess of 5 which can be used in lesser amounts are said to be quartz, silica, glass beads, and glass fibers. Samples prepared in accordance with the invention were tested for wear and compressive strength, but the patentee did not address the water stability problem.

U.S. Pat. No. 4,451,235 discloses an artifical dental root prepared by blending synthetic hydroxylapatite or calcined or sintered synthetic hydroxylapatite or a mixture thereof with polymerizable organic matrix and polymerizing the blend.

U.S. Pat. No. 4,491,453 discloses dental restorative light curable compositions comprising an inorganic filler, such as barium aluminum silicate; lithium aluminum silicate; strontium, lanthanum or tantalum glasses; silica; or quartz, and a photopolymerizable resin component containing, inter alia, a binder resin, such as a polymethacrylate. The filler may optionally, and preferably, be silanated, a process said to be "well known" in the art.

Thus although the prior art describes the use of organosilanes as keying agents to promote bonding between various particulate materials and polymeric resins, I have found that composites prepared from silanated ceramic hydroxylapatite and polymeric resins of the lower-alkyl polyacrylate class lack the strength and water resistance properties essential to stable dental restorative materials. I have further found that composites formed by pretreating particulate ceramic hydroxylapatite with a siliceous material, coating the silicated material with an organosilane and then polymerizing a mixture of the silicated and silanated material and polymeric resins of the lower-alkyl polyacrylate class possess superior strength and water resistance properties in comparison with corresponding samples lacking either the siliceous or organosilane coatings. I have also found that the improvement in water resistance properties is obtained if the ceramic hydroxylapatite is subjected to an etching process prior to treatment with the siliceous material comprising treatment either with dilute mineral acid or aqueous magnesium chloride or sequential treatment first with dilute mineral acid and then with aqueous magnesium chloride.

Although the composites of the present invention are particularly useful as dental restoratives, and such use is a particularly preferred aspect of the invention, they also find use as bone implants, for the preparation of orthopedic prosthetic devices and as bone cements.

SUMMARY OF THE INVENTION

In a process aspect, the invention relates to a process for preparing ceramic hydroxylapatite/polymeric resin composites which comprises coating particulate ceramic hydroxylapatite with a siliceous material, treating the thus silicated material with an organosilane, blending the thus treated particulate material with a polymerizable monomer or mixture of polymerizable monomers and polymerizing the blended mixture to form the composite.

In a composition aspect, the invention relates to composites comprising a mixture of particulate ceramic hydroxylapatite and a polymerizable monomer or mixture of polymerizable monomers wherein the particulate ceramic hydroxylapatite contains a first coat of a siliceous material and a second coat of an organosilane.

In another composition aspect, the invention relates to composites comprising particulate ceramic hydroxylapatite coated with a siliceous material and embedded, after treatment with an organosilane, by polymerization within a mass of polymeric resin.

In a further composition aspect, the invention relates to compositions useful as dental restoratives comprising two pastes for admixture with one another, one paste comprising a mixture of ceramic hydroxylapatite coated with a first coat of a siliceous material and a second coat of an organosilane, a polymerizable monomer or mixture of polymerizable monomers and a polymerization catalyst, the other paste comprising a mixture of ceramic hydroxylapatite similarly coated with a siliceous material and an organosilane, polymerizable monomer or monomers and a polymerization accelerator.

In a further composition aspect, the invention relates to compositions useful as dental restoratives comprising a mixture of particulate ceramic hydroxylapatite coated with a first coat of siliceous material and a second coat of an organosilane, a polymerizable monomer or mixture of polymerizable monomers and a catalyst for initiation of polymerization by exposure to light.

DETAILED DESCRIPTION OF THE PREFERRED EMBODIMENTS

More specifically, it has been found that composites prepared by coating particulate ceramic hydroxylapatite with a siliceous material, treating the thus coated particulate material with an organosilane and polymerizing a blend of the thus treated particulate ceramic hydroxylapatite with a polymerizable monomer or mixture of polymerizable monomers possess good strength and water resistance characteristics.

In a first step of producing the composites in accordance with the present invention, particulate ceramic hydroxylapatite is given a siliceous coating using either an aqueous solution of sodium silicate (usually defined by the formula $Na_2O \cdot xSiO_2$, where x, in commercially available solutions, is in the range from 1.6 to 3.75), sodium metasilicate or silicic acid generated from sodium silicate by ion exchange procedures.

The ceramic hydroxylapatite is prepared by sintering hydroxylapatite. The dense, polycrystalline hydroxylapatite ceramic known as durapatite which is described in U.S. Pat. No. 4,097,935 is preferred. I have also found that although suitable composites can be prepared using particulate ceramic hydroxylapatite up to about 40 μm, stronger composites are favored by use of a mixture of finer particles. Generally speaking, the strength of the composite is maximized by use of a combination of large and small sized particles so that the smaller sized particles will fill the spaces between the larger particles, thus maximizing the total volume occupied by the particulate material. It is therefore preferred to use a population of particulate ceramic hydroxylapatite having particle sizes selected from 2.4 (1–8)μm, 3.2 (1–8)μm, 5.3 (2.6–12)μm and 17 (5–33)μm, where the number outside the parentheses, e.g. 2.4, is the average size by population, i.e. half of the particles in the population are ≧2.4 μm and half are ≦2.4 μm. Five percent of the particles (by population) are of equal or smaller size than the first number in parentheses, e.g. 1, and five percent are of equal or greater size than the second number in parentheses, e.g. 8. In the description and the claims which follow the various samples of particulate ceramic hydroxylapatite used in the practice of the invention are identified by the above-noted average particle sizes, i.e. 2.4, 3.2, 5.3 and 17 μm. It will be understood, however, that in each instance, the material so-identified consists of a population of particle sizes as defined above for each of the average particle sizes.

Accordingly in a preferred aspect the particulate ceramic hydroxylapatite, having an average particle size of 3.2 μm and preferably about 5.3 μm, is stirred at ambient temperature in a solution containing from around 1 to 10 parts, and preferably from around 2 to 6 parts, of silicate or silicic acid per 100 parts of hydroxylapatite, i.e. from about 1 to 10 parts, and preferably from about 2–6 parts, per hundred of filler (phf), then collected, for example by filtration or centrifugation, and dried.

The surface of the particulate ceramic hydroxylapatite can optionally be activated, prior to silication, for example by etching with dilute mineral acid or by such etching followed by treatment with an aqueous solution of magnesium chloride. I have found that such surface activation produce substantial improvement in the water resistance properties of composites in comparison with composites prepared from unactivated material.

The silicated particulate ceramic hydroxylapatite prepared as described above is then treated with an organosilane which serves as a bonding or keying agent between the silicated hydroxylapatite and the polymerized resin. Examples of suitable organosilanes for such purpose are γ-methacryloxypropyltrimethoxysilane (produced and sold by Dow Corning as Z-6030 and by Union Carbide as A-174) or γ-methacryloxypropyl-tris-(β-methoxyethoxy)silane (produced and sold by Union Carbide as A-175). A preferred organosilane is Z-6030.

Silanation of the silicated particulate ceramic hydroxylapatite is carried out either by adsorption from a solution of the organosilane in an inert organic solent, such as cyclohexane, hexane or methanol, or by deposition from solution by evaporation of the solvent.

The preparation of the ceramic hydroxylapatite/polymeric resin composites is effected by mixing the silicated and silanized hydroxylapatite ceramic particulate material with a polymerizable monomer, or mixtures of two or more polymerizable monomers, that are capable of copolymerizing with the organosilane to produce stable chemical bonds thereto and polymerizing the mixture. Polymerization can be initiated either by irradiation, by heating or, preferably, chemically in the presence of a polymerization catalyst. Typical of such monomers are the lower-alkyl or lower-alkenyl esters of acrylic acid or methacrylic acid, such as methyl methacrylate, 2-hydroxyethyl methacrylate or allyl methacrylate, or cross linking monomers which have two or more polymerizable functional groups in the molecule. Typical of such polyfunctional monomers are ethylene glycol dimethacrylate, diethylene glycol dimethacrylate, triethylene glycol dimethacrylate (TEGMA), tetraethylene glycol dimethacrylate, polyethylene glycol dimethacrylate, trimethylolpropane trimethacrylate, 1,6 hexanediol dimethacrylate, 1,4-butanediol dimethacrylate, the diglycidyl dimethacrylate of bis-phenol A (bis-GMA), 2,2-bis-[4-(2-hydroxyethoxy)phenyl]propane dimethacrylate, 2,2-bis-[4-hydroxyphenyl]propane dimethacrylate or 2,2-bis-[4-(2-hydroxypropoxy)phenyl]propane dimethacrylate, all of which are known in the art.

Catalysts conventionally used for photo or irradiation initiated polymerization are a benzoin alkyl ether or a diketone, such as camphor quinone. Benzoyl peroxide or phosphite esters may be used to accelerate the cure which is usually completed in from 30 to 60 seconds. The materials are cured by an appropriate light source which produces radiation in the near ultraviolet region around 360 nm or in the visible light region of around 470 nm.

Heat initiated polymerization, as applied to composites for non-dental use, occurs at around 75°–100° C. and generally requires one or more hours to effect complete polymerization. Catalysts conventionally used in heat initiated polymerization are benzoyl peroxide or certain diacyl peroxides, for example diacetyl peroxide, bis(2,4-dichlorobenzoyl) peroxide or dilauryl peroxide.

When the composites are prepared by either photo or heat initiated polymerization, the particulate material is mixed with a polymerizable monomer or mixture of polymerizable monomers containing an appropriate polymerization initiator and the mixture then either irradiated with light or heated, as appropriate, to effect polymerization.

Catalysts useful for chemical initiation of polymerization are organic peroxides which decompose to form free radicals and include, for example, acyl peroxides, such as benzoyl peroxide, organic peracids, such as perbenzoic acid or perchlorobenzoic acid, lower-alkyl ketone peroxides, such as methyl ethyl ketone peroxide, peroxycarbonates, such as t-butyl peroxycarbonate, cumol peroxide, urea peroxide or butyl hydroperoxide.

The chemically cured composites of the invention are prepared by mixing the particulate material into each of two pastes, which are prepared and stored separately under refrigeration until use. One of the two pastes contains a polymerizable monomer and a polymerization catalyst of the type described above, and the other the same or a different monomer and a polymerization accelerator. Polymerization accelerators comprise various amines, well known in the art for the purpose, such as tributylamine, tripropylamine, N-lower-alkyl-N,N-dialkanolamines, such as N-methyl-N,N-diethanolamine, triethanolamine, N,N-bis-(2-hydroxyethyl)4-methylaniline, i.e. dihydroxyethyl-p-toluidine (hereinafter DHET), N,N-bis-(2-hydroxyethyl)-3,4-dimethylaniline, N,N-bis-(2-hydroxyethyl)-3,5-dimethylaniline, N-methyl-N-(2-hydroxyethyl)-4-methylaniline, N,N-dimethylaniline, N,N-dimethyl-p-toluidine (DMPT), N,N-dimethylaminoglutethimide (DMAG), N,N-di-(2-hydroxyethyl)-p-toluidine (DHEPT), N,N-di-(2-hydroxypropyl)-p-toluidine (DHPPT), N,N-dimethyl-sym-xylidine (DMSX), N,N-bis-(3-p-tolyloxy-2-hydroxypropyl)-sym-xylidine (BTX), 4-(N,N-dimethylamino)benzaldehyde (4-DMAB), 4-(N,N-dimethylamino)benzoic acid, tetramethylammonium 4-(N,N-dimethylamino)benzoate (TMADMAB), lithium 4-(N,N-dimethylamino)benzoate (LDMAB), 3-(N,N-dimethylamino)phenylacetic acid (DMAPAA), methyl 4-(N,N-dimethylamino)phenyl acetate, 4-(N,N-dimethylamino)pyridine and poly SAM-1 [a polyfunctional surface active amine prepared by polymerization of N-phenylglycine sodium salt and N-methyltoluidine with an epoxidized ortho-cresol-formaldehyde novolac; see Antonucci and Bowen, J. Dent. Res., 56, 937–942 (1977)].

The biocompatibility of the accelerator with the particular polymeric resins used will affect the choice of the accelerator, and the hardening time of the resin as well as the strength, color stability and water resistance properties of the resulting composite will be affected by the choice of the accelerator and the amount of accelerator used. Such variables can be readily determined by the person skilled in the art.

A preferred composition useful in the practice of the present invention comprises a catalyst paste containing a peroxide catalyst, TEGMA and bis-GMA and an activator paste comprising TEGMA, bis-GMA, and an amine activator. A preferred composition contains benzoyl peroxide (hereinafter BPO) as the catalyst and DHET as the accelerator. The ratios of the bis-GMA:-TEGMA in the catalyst and accelerator paste can vary from around 4:1 to around 1:4 and sufficient BPO and DHET are added to the two pastes to achieve the desired setting time. The setting time is best controlled by adjustments in the amount of DHET used in the activator paste, and particularly preferred compositions contain a ratio of bis-GMA:TEGMA:BPO in the catalyst paste of 7:3:0.1 and a ratio of bis-GMA:TEGMA:DHET in the accelerator paste of 7:3:0.05 which has a setting time of around 3 to 5 minutes.

The amount of particulate material in the resin composition can likewise be varied over wide limits. When used as dental restorative composites, the compositions can contain from around 40% to 80% particulate material based on the total weight of the composite, and when used for other than dental restorative purposes, particulate levels as low as 20% may be used. Generally speaking, the greater the weight (volume) fraction of the particulate matter in the composite the stronger the composite, provided the particulate matter is adequately adherent to the cured resin. The keying agent provides improved adhesion. As indicated above, the strength of the composite is maximized by maximizing particulate loading, and this is accomplished by careful choice of the size distribution of the particulate in order to achieve close packing. A preferred chemically activated composite is prepared by mixing sufficient particulate with each of the catalyst and activator pastes to provide about 70% particulate loading in the catalyst and activator pastes and then mixing equal weights of the two pastes to provide the desired amount of particulate material in the final composite.

The practice of the invention is further illustrated by the following exemplary disclosure.

PREPARATION OF THE COMPOSITIONS OF THE INVENTION

Example I. Optional Surface Treatment Procedures

1. Acid Etching

To 200 ml of a 0.3% solution of hydrochloric acid in distilled water in a glass flask containing a TEFLON ® stirring bar were added 12 g of 5.3 μm ceramic hydroxylapatite powder. The mixture was stirred at room temperature for 20 minutes, centrifuged, and the sediment washed three times with 90 ml of distilled water followed by one washing with 80 ml of methanol by stirring the moist sediment with the solvent, centrifuging and discarding the supernatant. After completion of the last washing, the powder was dried under vacuum.

2. Magnesium Chloride

To a solution containing 8 g of magnesium chloride hexahydrate in 100 ml of distilled water were added 20 g of 5.3 μm ceramic hydroxylapatite powder. The slurry was stirred with a TEFLON ® bar in a glass flask for ten minutes at room temperature, then centrifuged and the sediment washed four times with 80 ml of distilled water by centrifugation and decantation and then dried under vacuum.

Example II. Silication of Ceramic Hydroxylapatite

1. Silication with Aqueous Sodium Silicate

A commercial 37.1% aqueous solution (1.4 ml, 2.0 g) of $Na_2O:3.37SiO_2$ was passed through a MILLEX ™- GS 0.22 μm filter unit attached to a syringe into 100 ml of stirred distilled water. From the resulting solution 15 ml were removed and diluted with 35 ml of distilled water. To the diluted solution, containing 0.11 g (2.2 phf) of sodium silicate and at pH 10.5, were added 5.0 g of 5.3 μm ceramic hydroxylapatite powder which had been etched with hydrochloric acid. The mixture was loosely covered and stirred at room temperature for 17 hours, then centrifuged and the sediment washed three times with 40 ml of distilled water by stirring, centrifugation and decantation. The washed solid was then dried under vacuum at room temperature and finally heated in an oven at 155° C. for 2 hours.

2. Silication with Silicic Acid

A solution of 2.4 g of sodium metasilicate ($Na_2SiO_3 \cdot 5H_2O$) in 50 ml of distilled water was passed through a column of 47 ml of REXYN ™ 101 ($H^+$) ion exchange resin (Fisher Scientific Co., Product No. R-231) at a flow rate of about 2 ml/min. Collection of eluate was stopped when the pH had increased from 2.2 to about 5.5. The total eluate (91 ml) was thoroughly mixed, and 40 ml (corresponding to 5 phf based on the original amount of sodium silicate) was diluted with 60 ml of distilled water and 20 g of 5.3 μm ceramic hydroxylapatite powder was added. Before addition of the latter, the pH was 3.2 and after the hydroxylapatite/silicic acid solution had been stirred for 7 minutes, the pH was about 6.0. Stirring at room temperature was continued for a total of 2 hours, after which the pH was 6.0. The mixture was then centrifuged and the sediment washed four times with 80 ml of distilled water by stirring, centrifugation and decantation. The solid was dried under vacuum at room temperature and then heated a 155° C. for 2 hours.

3. Silication with Aqueous Sodium Metasilicate 0.40 g of crystalline $Na_2SiO_3 \cdot 5H_2$, "sodium metasilicate", were dissolved in 10 ml of distilled water. An additional 60 ml of distilled water were added and the solution was stirred for 3 minutes. Then 10 g of 5.3 μm ceramic hydroxylapatite powder were added, and the mixture was stirred at room temperature for 2.5 hours, at which time the pH was 12. The pH was lowered to about 6.8 with hydrochloric acid. Stirring at room temperature was continued for another 13.3 hours. The mixture was then centrifuged, and the sediment was washed four times with 40 ml portions of distilled water by suspension, centrifugation and decantation. The washed solid was then placed under vacuum for 3 hours to remove most of the residual water and then heated at 155°–160° C. for 1 hour.

Example III. Silanation of Silicated Ceramic Hydroxylapatite

1. By Adsorption from a Cyclohexane Solution

To 100 ml of cyclohexane in a glass vessel were added 0.25 g of Z-6030. The solution was stirred for about 1 minute and then treated with 0.25 g of n-propylamine. The solution was stirred for an additional 5 minutes, then one drop (about 35 mg) of water was added and the mixture stirred for an additional five minutes. At the end of this period the water was still present in the form of tiny droplets, and stirring was continued as 1.95 g of 5.3 μm ceramic hydroxylapatite powder (previously silicated with a solution containing 4 phf of sodium metasilicate) were added. Stirring was stopped after 17 hours, at which point all water had disappeared, and the slurry was centrifuged. The sediment was washed three times with 80 ml of methanol by stirring, centrifugation and decantation and then dried under vacuum and heated at 120° C. for 1 hour.

2. By Deposition from Solution

In a 500 ml round bottom flask were placed, in order, 100 ml of methanol, 1 drop of distilled water, 0.20 g of Z-6030, 0.20 g of n-propylamine and 4.0 g of 5.3 μm ceramic hydroxylapatite powder, previously silicated with a solution containing 2.2 phf of $Na_2O:3.37SiO_2$, the addition of water, Z-6030 and n-propylamine being followed in each instance by stirring magnetically for 1 minute. The mixture was then stirred magnetically for about 4 minutes after addition of the hydroxylapatite powder. The flask was then placed on a rotary evaporator in a water bath at 20° C. After 30 minutes of rotation under vacuum, about 75% of the liquid had evaporated, and the bath temperature had fallen to 16° C. The bath temperature was raised to 40° C. over the next 10 minutes, during which time all of the liquid disappeared, and was then maintained at 40° C. for an additional 10 minutes. The flask and contents were then heated in an oven at 110°–120° C. for 1 hour.

Example IV. Preparation of Composites

A resin/BPO stock catalyst mixture was prepared by dissolving 0.1 part of BPO in 3 parts of TEGMA and using that solution to dilute seven parts of bis-GMA to prepare a 73:0.1 mixture (all parts by weight) of bis-GMA:TEGMA:BPO. A bis-GMA/TEGMA/DHET (7:3:0.05) accelerator solution was prepared in the same way. Both solutions were kept under refrigeration until needed for further use.

In order to prepare a paste having a powder loading of 70% by weight, 0.215 g of the catalyst (BPO) liquid were mixed by hand with 0.5 g of ceramic hydroxylapatite powder on a watch glass for 5 minutes using a nylon spatula. The same procedure was used to prepare a paste of 0.215 g of the accelerator (DHET) liquid and 0.5 g of ceramic hydroxylapatite powder. Equal amounts of the two pastes were mixed with a plastic spatula at room temperature for 30 seconds to provide a mixture composed of 70% by weight of hydroxylapatite. The mixture was then loaded into mold cavities placed on a sheet of Mylar film, about 0.2 mm thick, so that the composite would be in contact with the Mylar at the bottom of the cavity, and a second sheet of Mylar film was placed in contact with the composite at the top of the mold cavity. The mold was then sandwiched between two sheets of stiff plastic, about 5 mm thick, and pressure was applied to the sandwich by means of spring clips. The mold was then transferred to a chamber kept at 37° C. for 15 minutes. After removal from the chamber, excess composite was ground off from the edges of the resulting molded composite test cylinders using water cooling and the samples then placed either in dry vials or in vials filled with distilled water, in accordance with further testing needs, and the vials stored in an oven at 37° C.

Physical properties of composites which were prepared in accordance with the invention or for comparative test purposes were determined by measurement of their transverse strength (TS), compressive strength (CS) or diametral tensile strength (DTS) using procedures to be described hereinafter. Specimens intended for transverse strength measurement were bars 24×2×2 mm prepared in polyethylene (or polypropylene) molds, and specimens intended for compressive strength or diametral tensile strength determination were cylinders 3 mm in diameter x 6 mm long prepared in stainless steel molds.

Preparation of Comparative Samples

For purposes of comparison, unsilicated ceramic hydroxylapatite was silanated, and resin/particulate composites were prepared from the thus treated particulate materials. Silanation was accomplished as follows:

Comparative Sample 1

(from ceramic hydroxylapatite silanated with Z-6030)

In a 500 ml round bottom flask were placed, in order, 100 ml of methanol, 0.117 g (three drops) of distilled water, 1.0 g of Z-6030 and 1.0 g of n-propylamine. The flask was swirled by hand to mix the contents, and then 0 g of 17 μm ceramic hydroxylapatite powder were added. The flask was placed on a rotary evaporator at a bath temperature of 30° C. for 10 minutes after which time most of the liquid had evaporated. The bath temperature was raised to 50° C. over 14 minutes, maintained at 50° C. for 10 minutes and the flask and contents then heated in an oven at about 20° C. for 1 hour.

Comparative Sample 2

(from ceramic hydroxylapatite silanated with Z-6032)

In a 500 ml round bottom flask were added, in order, 00 ml of methanol, 28 mg of glacial acetic acid, 0.117 g (three drops) of distilled water and 2.5 g of Z-6032. The flask was swirled by hand to mix the contents and then 20 g of 17 μm ceramic hydroxylapatite powder were added. The flask was placed on a rotary evaporator at a bath temperature of 30° C. After 20 minutes most of the liquid had been removed. The bath temperature was raised to 54° C. over a period of 15 minutes and maintained at 50° C. for the next 50 minutes. The solid was removed from the flask, crushed with a sintered corundum mortar and pestle and placed in an oven. The oven temperature was raised from 80° C. to 110° C. over 30 minutes and then maintained at 115° C. for 1 hour.

Comparative Sample 3

(from ceramic hydroxylapatite silanated with Z-6020)

A cloudy solution of 4.0 g of Z-6020, N-[3-(trimethoxysilyl)propyl]-1,2-ethanediamine (sold as Z-6020 by Dow Corning), in 80 ml of hexane was stirred for 15 minutes, the solution was transferred to another glass vessel and 10 g of 3.2 μm ceramic hydroxylapatite powder were added. The mixture was stirred for 61 hours, centrifuged, and the sediment washed two times with 80 ml of hexane by stirring, centrifugation and decantation and then dried under vacuum and heated at 120° C. for 1 hour.

Comparative Sample 4

(from silica powder silanated with Z-6030)

In a 500 ml round bottom flask were placed, in order, 100 ml of methanol, 3 drops of distilled water and 1.0 g of Z-6030. The flask was swirled by hand to mix the contents and then 1.0 g of n-propylamine was added and the flask swirled again. To the solution were then added 20 g of silica powder (Fisher Scientific Co. Product No. S-153; "about 240 mesh"), and the slurry was placed on a rotary evaporator. The bath was kept at 20° C. for 30 minutes, at 30° C. for the next 5 minutes (after which the flask was dry), and then at 42°–45° C. for 10 minutes. The flask containing the dried particulate matter was then placed in an oven at 120° C. for 1 hour.

Measurement of Properties of Composites

Diametral tensile strength (DTS), transverse strength (TS) and compressive strength (CS) measurements were determined at ambient temperature and humidity with an Instron dynamic testing instrument using a cross-head speed of 0.1 cm/min. (DTS and CS) or 0.05 cm/min. (TS). Samples stored in water were wiped with absorbent paper to remove surface water before testing. The size and method of preparation of the specimens was described previously. The three-point beam procedure described by Edwards, Jacobsen and Williams, J. Dent. Res., 62, 1086 (1983) was used for the TS measurements. For the DTS measurements, the cylindrical specimens were placed, with their axes perpendicular to the direction of loading, on the hard, flat metal loading plate and compressed until the sample split in half along a diameter as illustrated by Coury, Miranda and Duncanson, J. Prosthetic Dent., 45, 296 (1981); the formula given by these authors was used to calculate the DTS from the compression load at failure. No padding material, such as those described by Thomas, Doremus, Jarcho and Salsbury, J. Mat. Sci., 15,891 (1980), was used between the sample and the loading plates. For the CS measurements, the cylindrical specimens were placed on the loading plate with their axes parallel to the direction of loading.

For all tests, 3 to 6 specimens (as indicated in the tables) were used for each determination, and the values were recorded as the mean ± mean deviation of individual measurements on the 3 t o 6 specimens. If one of the measurements was 20% or more below the mean, it was discarded and a new mean of the remaining measurements calculated. The mean ± mean deviation values given in the tables below are followed in parentheses by the number of measurements used to calculate the mean over the total number of specimens measured in an individual test, e.g. 6/6 or 5/6.

In order to determine the effect of the use of an organosilane as a keying agent between the particulate hydroxylapatite itself and the resin, several composites composed of 70 weight percent of 2.4 μm Z-6030-treated ceramic hydroxylapatite powder and the balance a 7:3 BPO/DHET-cured mixture of bis-GMA:-TEGMA were prepared as described above in Example IV, the samples were stored in water at 37° C. and the TS and CS were determined at intervals of 1 day, 7 days and 30 days. The silanized hydroxylapatite was either heated after silane coating or not as indicated, and two samples were etched with hydrochloric acid before silanation. The results obtained are given in Table 1.

TABLE 1

| Experiment | Treatment | Agent | Transverse Strength (MPa) | | | Compressive Strength (MPa) | | |
|---|---|---|---|---|---|---|---|---|
| | | | 1 Day | 7 Days | 30 days | 1 Day | 7 Days | 30 days |
| 1A | None | None | 49.7 ± 4.7 (4/4) | 39.0 ± 1.9 (4/4) | 44.4 ± 3.9 (4/4) | 139 ± 4.8 (4/4) | 141 ± 5.3 (4/4) | 141 ± 4.0 (3/3) |
| 1B | None | Z-6030 (a) | 48.2 ± 1.8 (4/4) | 40.5 ± 1.8 (4/4) | 42.0 ± 2.0 (4/4) | 141 ± 4.8 (4/4) | 145 ± 5.0 (4/4) | 138 ± 2.0 (4/4) |
| 1C | None | Z-6030 (b) | 51.8 ± 4.0 (4/4) | 46.5 ± 4.2 (4/4) | 42.8 ± 2.9 (4/4) | 151 ± 4.8 (4/4) | 141 ± 2.3 (4/4) | 143 ± 5.0 (4/4) |
| 1D | HCl Etch | Z-6030 (a) | 46.8 ± 1.5 (4/4) | 36.3 ± 2.1 (4/4) | 38.9 ± 1.2 (4/4) | 112 ± 12.2 (3/3) | 131 ± 5.5 (4/4) | 123 ± 2.3 (4/4) |
| 1E | HCl Etch | Z-6030 (b) | 40.5 ± 3.2 (4/4) | 41.5 ± 4.1 (4/4) | 40.7 ± 3.0 (4/4) | 125 ± 7.0 (4/4) | 128 ± 10.7 (3/3) | 110 ± 16.1 (4/4) |

(a) Not heated after silane coating
(b) Heated at 110–120° C. for 0.5 to 1.0 hour after silane coating The picture that clearly emerges from the above data is that the silane coat produces no appreciable increase in TS and CS over the unsilanated controls.

In order to compare the effect of an organosilane keying agent between hydroxylapatite (HA) and resin and between silica and resin, composites composed of 70 weight percent of 17 μm ceramic hydroxylapatite powder or 60 μm silica, either uncoated or coated with Z-6030 or Z-6032 (Comparative Samples 1, 2 and 4 above) and the balance a 7:3 BPO/DHET-cured mixture of bis-GMA:TEGMA were prepared as described above in Example IV, stored for one day dry at 37° C., the DTS and CS determined for each composite and the percent increase in DTS or CS over composites prepared from unsilanized hydroxylapatite or silica were calculated, i.e. % Increase=(DTS Silanized-DTS Unsilanized)/DTS Unsilanized×100. The results obtained are set forth in Table 2.

percent of 3.2 μm ceramic hydroxylapatite coated with the organosilanes 3-aminopropyltriethoxysilane (sold as A-1100 by Union Carbide) and N-[3-(trimethoxysilyl)-propyl]-1,2-ethanediamine (Z-6020; Comparative Sample 3 above) and the balance a BPO/DHET-cured 7:3 bis-GMA:TEGMA mixture were prepared as described in Example IV and the DTS of the samples determined after varying periods of dry or wet storage at 37° C. For control purposes, samples of test cylinders composed of resin alone and of composites prepared from uncoated ceramic hydroxylapatite were similarly prepared and tested. The percent increase in DTS for the samples over the DTS values of the corresponding uncoated 7, 9 or 14 day (dry or wet) stored samples was also calculated, i.e. % Increase=(DTS Dry - DTS Dry of Control)/DTS Dry of Control×100 or % Increase=(DTS Wet - DTS Wet of Control)/DTS Wet of Control×100. The results are set forth in Table 3.

TABLE 2

| Experiment | Powder | Keying Agent | DTS (MPa) | % Increase in DTS Over Uncoated Powder | CS (MPa) | % Increase in CS Over Uncoated Powder |
|---|---|---|---|---|---|---|
| 2A | Resin alone | — | 31.6 ± 3.2 (3/4) | — | — | — |
| 2B | HA | None | 17.5 ± 0.9 (3/3) | — | — | — |
| 2C | HA | Z-6032 | 18.4 ± 0.7 (5/5) | 5 | — | — |
| 2D | HA | Z-6030 | 19.6 ± 1.7 (6/6) | 12 | — | — |
| 2E | Silica | None | 15.3 ± 1.3 (3/3) | — | 107 ± 2.0 (3/3) | — |
| 2F | Silica | Z-6030 | 29.8 ± 2.4 (3/3) | 95 | 153 ± 9.7 (3/3) | 43 |

TABLE 3

| Experiment | Keying Agent | Weathering Time at 37° C. | DTS (MPa) | % Loss of DTS Due to Water | % Increase in DTS Over Uncoated Control |
|---|---|---|---|---|---|
| 3A | Resin alone | 7 days dry | 37.3 ± 1.0 (6/6) | — | — |
| 3B | Resin alone | 7 days wet | 33.4 ± 2.4 (6/6) | 10 | — |
| 3C | Uncoated | 7 days dry | 22.6 ± 1.3 (5/6) | — | — |
| 3D | Uncoated | 7 days wet | 18.8 ± 1.4 (6/6) | 17 | — |
| 3E | 40 phf A-1110 (a) | 7 days dry | 26.3 ± 1.9 (5/6) | — | 16 |
| 3F | 40 phf A-1110 (a) | 7 days wet | 20.6 ± 0.4 (6/6) | 22 | 10 |
| 3G | Z-6020 (b) | 1 day dry | 23.4 ± 0.9 (4/6) | — | — |
| 3H | Z-6020 (b) | 14 days dry | 23.8 ± 1.9 (6/6) | — | 5 |
| 3I | Z-6020 (b) | 14 days wet | 17.5 ± 0.5 (6/6) | 26 | −7 |
| 3J | Z-6020 (c) | 1 day dry | 25.0 ± 2.1 (6/6) | — | — |
| 3K | Z-6020 (c) | 9 days dry | 27.6 ± 3.2 (6/6) | — | 22 |
| 3L | Z-6020 (c) | 9 days wet | 15.6 ± 1.0 (6/6) | 43 | −17 |
| 3M | Z-6020 (d) | 1 day dry | 26.7 ± 2.5 (6/6) | — | — |
| 3N | Z-6020 (d) | 7 days dry | 29.8 ± 1.6 (4/6) | — | 32 |
| 3O | Z-6020 (d) | 7 days wet | 15.5 ± 1.4 (5/5) | 48 | −18 |

(a) Applied as 5% solution in hexane with stirring for 25 hours and washed with hexane.
(b) Applied as solution in hexane with stirring for 3 hours.
(c) Applied as solution in hexane with stirring for 61 hours.
(d) Applied as solution in hexane with stirring for 61 hours and powder heated for 1 hour at 120° C.

As shown by the data, silanation of hydroxylapatite with Z-6032 and Z-6030 produced an increase in DTS over uncoated hydroxylapatite of 5% and 12%, respectively, whereas silanation of silica with Z-6030 produced a 95% increase in DTS and a 43% increase in CS over unsilanized silica.

In order to determine the effect of an organosilane coat on hydroxylapatite on the stability to water of composites of hydroxylapatite with bis-GMA:TEGMA resins, a number of composites composed of 70 weight These results show that weathering of all samples in water, including even the non-filler containing control, caused an overall reduction in strength of the composites ranging from 10% to 48%. Loss of strength due to weathering of composites prepared from silane coated hydroxyl apatite varied from 22% to 48%.

A number of composites within the ambit of the present invention composed of 70 weight percent of 5.3 μm ceramic hydroxylapatite treated first with either an aqueous Na$_2$O:3.37 SiO$_2$ solution, an aqueous solution of Na$_2$SiO$_3$·5H$_2$O, or an aqueous silicic acid solution followed in each case by a coating of Z-6030 and the balance a BPO/DHET-cured 7:3 mixture of bis-GMA:-TEGMA resin were prepared and the DTS of the composites determined after one day dry storage at 37° C. For comparative purposes, composites lacking both the silication and silanation coat (Experiment 4B) and silicated but lacking the silanation coat (Experiments 4C, 4E, 4G, 4I, 4L, 4O, 4R, 4T and 4V) were also similarly prepared and tested. The test results are set forth in Table 4 below.

TABLE 4

| Experiment | Powder Pretreatment | Silicate Coating Procedure | Coated with Z-6030 (a) | DTS (MPa) | % Increase in DTS Over Unsilicated/Unsilanated Control | % Increase in DTS Over Silicated/Unsilanated Control |
|---|---|---|---|---|---|---|
| 4A | Resin alone - no filler | — | — | 31.5 ± 1.6 (6/6) | — | — |
| 4B | None | Unsilicated control | No | 18.7 ± 1.0 (5/6) | — | — |
| 4C | None | (b) | No | 18.8 ± 1.5 (6/6) | 1 | — |
| 4D | None | (b) | Yes. Powder not washed | 26.6 ± 1.4 (6/6) | 42 | 41 |
| 4E | None | (c) | No | 21.3 ± 1.6 (6/6) | 14 | — |
| 4F | None | (c) | Yes. Powder not washed | 24.9 ± 1.1 (6/6) | 33 | 17 |
| 4G | HCl Etch | (d) | No | 18.3 ± 1.7 (4/6) | −2 | — |
| 4H | HCl Etch | (d) | Yes. Powder not washed | 24.2 ± 1.8 (6/6) | 29 | 32 |
| 4I | HCl Etch | (e) | No | 19.4 ± 0.9 (4/6) | 4 | — |
| 4J | HCl Etch | (e) | Yes. Powder not washed | 29.1 ± 3.2 (6/6) | 56 | 50 |
| 4K | HCl Etch | (f) | Yes. Powder washed in methanol | 30.2 ± 1.9 (6/6) | 61 | 56 |
| 4L | None | (g) | No | 18.3 ± 1.2 (6/6) | −2 | — |
| 4M | None | (g) | Yes. Rotary procedure. Powder not washed. | 18.1 ± 1.3 (5/6) | −3 | −1 |
| 4N | None | (g) | Yes. Rotary procedure. Powder washed with methanol | 21.9 ± 2.1 (4/6) | 17 | 20 |
| 4O | None | (h) | No | 28.2 ± 0.8 (4/6) | 51 | — |
| 4P | None | (h) | Yes. Rotary procedure. Powder not washed. | 26.4 ± 2.2 (5.6) | 41 | −6 |
| 4Q | None | (h) | Yes. Suspension procedure. Washed with methanol. | 24.5 ± 1.7 (6/6) | 31 | −13 |
| 4R | (1) HCl Etch, (2) MgCl$_2$ | (i) | No | 24.0 ± 1.3 (6/6) | 28 | — |
| 4S | (1) HCl Etch, (2) MgCl$_2$ | (i) | Yes. Rotary procedure. Powder not washed. | 25.2 ± 2.4 (5/6) | 35 | 5 |
| 4T | None | (j) | No | 17.2 ± 1.6 (5/6) | −8 | — |
| 4U | None | (j) | Yes. Rotary procedure. Powder not washed. | 20.8 ± 2.6 (6/6) | 11 | 21 |
| 4V | None | (k) | No | 14.6 ± 2.2 (6/6) | −22 | — |
| 4W | None | (k) | Yes. Rotary procedure. Powder not washed. | 24.2 ± 1.1 (6/6) | 29 | 66 |
| 4X | None | (l) | Yes. Rotary procedure. Powder not washed. | 25.7 ± 0.6 (6/6) | 37 | — |

(a) In all cases except Experiment 4Q, the rotary evaporation procedure described in Example III.2 was used to coat with 5 phf of Z-6030. In some cases the dry powder in the flask was washed with methanol before it was heated at 120°. For Experiment 4Q, the hexane suspension procedure described in Example III.1 was used.
(b) 0.74 phf Na$_2$O:3.37 SiO$_2$ as 0.1% solution at natural pH ($\geq$9), stirred 17 hours with powder.
(c) 6.7 phf Na$_2$O:3.37 SiO$_2$ as 1% solution at natural pH ($\geq$11), stirred 19 hours with powder.
(d) 0.37 phf Na$_2$O:3.37 SiO$_2$ as 0.05% solution at natural pH (9), stirred 17 hours with powder.
(e) 2.2 phf Na$_2$O:3.37 SiO$_2$ as 0.2% solution at natural pH (10.5), stirred 17 hours with powder.
(f) 2.2 phf Na$_2$O:3.37 SiO$_2$ as 0.2% solution at natural pH (10), stirred 15 hours with powder.
(g) 4 phf Na$_2$SiO$_3$·5H$_2$O as 0.6% solution pH was adjusted from 12.2 to 6.8 with HCl, then stirred with powder for 1 hour.
(h) 4 phf Na$_2$SiO$_3$·5H$_2$O as 0.6% solution at natural pH (12) stirred with powder for 2.5 hours. The pH was adjusted to 6.8 with HCl and the mixture stirred for 13 hours.
(i) 4 phf Na$_2$SiO$_3$·5H$_2$O as 0.6% solution at natural pH (12) stirred with powder for 2.5 hours. The pH was adjusted to 6.8 with HCl and the mixture was stirred for 16 hours.
(j) Ion exchange gave silicic acid solution. 2 phf (based on weight of Na$_2$SiO$_3$·5H$_2$O) before exchange as 0.6% solution at natural pH (3.5) was adjusted to pH 8.5 with KOH. Stirred with powder for 25 minutes.
(k) Ion exchange gave silicic acid solution. 2 phf (based on weight of Na$_2$SiO$_3$·5H$_2$O before exchange) as 0.6% solution at natural pH (3.5) was adjusted to pH 8.5 with KOH. Powder was stirred for 25 minutes in this solution, washed with water and then stirred for 25 minutes with 16 phf (based on weight of Na$_2$SiO$_3$·5H$_2$O before exchange) as 2.7% solution at pH 7.0.
(l) Ion exchange gave silicic acid solution. 5 phf (based on weight of Na$_2$SiO$_3$·5H$_2$O before exchange) as 1% solution at natural pH (3.2) was stirred with powder for 2 hours. The pH after 7 minutes and after 2 hours was 6.

For the sake of clarity, the results shown in Table 4 are recapitulated in Table 4 (Summary) below, individual results being identified by experiment numbers used in Table 4. The results are summarized in columns A, B and C in the summary where the numbers in column A represent the % increase in DTS of silicated/silanated composites of the invention over the unsilicated/unsilanated control (described in Experiment 4B); the numbers in column B represent the % increase in DTS of silicated/silanated composites of the invention over the appropriate silicated/unsilanated control (described in Experiments 4C, 4E, 4G, 4I, 4L, 4O, 4R, 4T and 4V); and the numbers in column C represent the % increase in DTS of silicated/unsilanated composites over the unsilicated/unsilanated control (described in Experiment 4B). In each instacce the particular experiment number used in Table 4 above is given in parentheses.

TABLE 4

| | (Summary) | |
|---|---|---|
| A | B | C |
| 42 (4D) | 41 (4D) | 1 (4C) |
| 33 (4F) | 17 (4F) | 14 (4E) |
| 29 (4H) | 32 (4H) | −2 (4G) |
| 56 (4J) | 50 (4J) | 4 (4I) |
| 61 (4K) | 56 (4K) | |
| −3 (4M) | −1 (4M) | −2 (4L) |
| 17 (4N) | 20 (4N) | |
| 41 (4P) | −6 (4P) | 51 (4O) |
| 31 (4Q) | −13 (4Q) | |
| 35 (4S) | 5 (4S) | 28 (4R) |
| 11 (4U) | 21 (4U) | −8 (4T) |
| 29 (4W) | 66 (4W) | −22 (4V) |
| 37 (4X) | | |

These results show that composites prepared according to the invention generally produce an increase in DTS of around 11–61% in comparison with the control composite prepared from unsilicated/unsilanated material and an increase in DTS of around 17–66% in comparison with the appropriate control composite prepared from silicated/unsilanated material. The results obtained in Experiments 4M, 4P, 4Q and 4S appear to indicate that the use of solutions of silicate prepared from crystalline $Na_2SiO_3.5H_2O$ is less effective in producing the desired strength property in the composites. (See footnotes (g), (h), and (i) of Table 4.) In contrast, composites prepared from silicated/unsilanated particulate ceramic hydroxylapatite generally produce a negligible increase in DTS in comparison with the control composite prepared from unsilicated/unsilanated material.

The stability to weathering of composites prepared in accordance with the invention was determined by subjecting composites composed of 70 weight percent of silicated and Z-6030 coated 5.3 μm ceramic hydroxylapatite and the balance a BPO/DHET-cured 7:3 mixture of bis-GMA:TEGMA to exposure to water at 37° C. for varying periods of time. For this purpose, a pool of samples was prepared on day 0; 1 group selected at random from the pool was stored dry at 37° C. for 7 days, and a second group was simultaneously stored in water at 37° C. From the second group, 6 specimens were removed at 7 days for testing for DTS, and another 6 were removed at 28–29 days.

For comparative purposes, other composites similarly composed but lacking an organosilane coating were prepared, pooled and treated similarly for DTS determination. The loss in DTS following weathering was then calculated as percent loss [DTS dry at 7 days - DTS wet/DTS dry at 7 days×100]. The results obtained are given in Table 5. In certain cases the ceramic hydroxylapatite was etched with hydrochloric acid or treated with magnesium chloride prior to siliceous coating. In all cases, silanation with Z-6030 was carried out using the rotary procedure described in Example III 2.

TABLE 5

| Experiment | Powder Pretreatment | Siliceous Coating | Z-6030 Coating | Weathering Time at 37° C. | DTS (MPa) | % Loss of DTS Due to $H_2O$ |
|---|---|---|---|---|---|---|
| 5A | None | 0.74 phf $Na_2O:3.37SiO_2$ pH ≧ 9 | Yes | 7 days dry | 29.1 ± 3.1 (6/6) | — |
| 5B | None | 0.74 phf $Na_2O:3.37SiO_2$ pH ≧ 9 | Yes | 7 days wet | 25.4 ± 1.5 (6/6) | 13 |
| 5C | None | 0.74 phf $Na_2O:3.37SiO_2$ pH ≧ 9 | Yes | 29 days wet | 21.7 ± 0.9 (6/6) | 25 |
| 5D | None | 6.7 phf $Na_2O:3.37SiO_2$ pH ≧ 11 | Yes | 7 days dry | 26.3 ± 2.7 (6.6) | — |
| 5E | None | 6.7 phf $Na_2O:3.37SiO_2$ pH ≧ 11 | Yes | 7 days wet | 22.9 ± 2.0 (5/6) | 13 |
| 5F | HCl Etch | 2.2 phf $Na_2O:3.37SiO_2$ pH 10.5 | Yes | 7 days dry | 31.2 ± 2.2 (6/6) | — |
| 5G | HCl Etch | 2.2 phf $Na_2O:3.37SiO_2$ pH 10.5 | Yes | 7 days wet | 27.0 ± 1.7 (6.6) | 13 |
| 5H | HCl Etch | 2.2 phf $Na_2O:3.37SiO_2$ pH 10.5 | Yes | 28 days wet | 21.8 ± 1.5 (5/6) | 30 |
| 5I | None | 4 phf $Na_2SiO_3.5H_2O$ pH 12 initially then reduced to 6.8 | No | 7 days dry | 28.6 ± 1.1 (5/6) | — |
| 5J | None | 4 phf $Na_2SiO_3.5H_2O$ pH 12 initially then reduced to 6.8 | No | 7 days wet | 21.8 ± 2.0 (5/5) | 24 |
| 5K | None | 4 phf $Na_2SiO_3.5H_2O$ pH 12 initially then reduced to 6.8 | Yes | 7 days dry | 34.2 ± 0.4 (5/6) | — |
| 5L | None | 4 phf $Na_2SiO_3.5H_2O$ pH 12 initially | Yes | 7 days wet | 22.6 ± 0.8 (5.6) | 34 |

TABLE 5-continued

| Experiment | Powder Pretreatment | Siliceous Coating | Z-6030 Coating | Weathering Time at 37° C. | DTS (MPa) | % Loss of DTS Due to $H_2O$ |
|---|---|---|---|---|---|---|
| 5M | None | then reduced to 6.8 4 phf $Na_2SiO_3.5H_2O$ ph 12 initially then reduced to 6.8 | Yes | 29 days wet | 17.2 ± 0.9 (6/6) | 50 |
| 5N | (1) HCl Etch (2) $MgCl_2$ | 4 phf $Na_2SiO_3.5H_2O$ | Yes | 7 days dry | 24.7 ± 1.9 (5/6) | — |
| 5O | (1) HCl Etch (2) $MgCl_2$ | 4 phf $Na_2SiO_3.5H_2O$ | Yes | 7 days wet | 22.7 ± 1.4 (5/6) | 8 |
| 5P | (1) HCl Etch (2) $MgCl_2$ | 4 phf $Na_2SiO_3.5H_2O$ | Yes | 28 days wet | 20.4 ± 0.6 (5/5) | 17 |

These results show that silanation of the silicate coated ceramic hydroxylapatite prepared in accordance with the present invention provides approximately a twofold improvement in loss of DTS, as measured after 7 days exposure to water, over composites prepared from unsilanated ceramic hydroxylapatite, irrespective of whether the hydroxylapatite is pre-etched with hydrochloric acid or not. (Compare, for example, the results of Experiments 5I-5J with the results of Experiments 5A-5B, 5D-5E and 5F-5G.) Even more dramatic improvement in water resistance of composites in accordance with the invention is achieved by pre-etching the ceramic hydroxylapatite with hydrochloric acid and treatment of the etched powder with magnesium chloride. (Compare the results of Experiments 5I-5J with the results of Experiments 5N-5O.)

I claim:

1. A process for preparing ceramic hydroxylapatite/polymeric resin composites which comprises coating particulate ceramic hydroxylapatite with a siliceous material selected from the group consisting of sodium silicate, sodium metasilicate and silicic acid by stirring said hydroxylapatite with a solution of said siliceous material, treating the silicated material with an organosilane selected from the group consisting of γ-methacryloxypropyltrimethoxysilane and γ-methacryloxypropyl-tris-(β-methoxyethoxy) silane by adsorption or deposition thereof from a solution of said organosilane in an inert organic solvent, blending the thus treated particulate material with a polymerizable monomer or mixture of polymerizable monomers and polymerizing the blended mixture.

2. The process according to claim 1 wherein said polymerizable monomers comprise a mixture of bis-GMA, 2,2-bis-propane dimethacrylate and TEGMA, triethylene glycol dimethacrylate.

3. The process according to claim 2 which comprises blending 70 weight percent of said treated particulate material with a chemically curable 7:3 mixture of said bis-GMA:TEGMA.

4. The process according to claim 3 wherein said organosilane is γ-methacryloxypropyltrimethoxysilane.

5. The process according to claim 4 wherein the particles of said ceramic hydroxylapatite have an average size of 5.3 μm.

6. The process according to claim 5 wherein said ceramic hydroxylapatite particles are activated by etching, prior to silication, by stirring said hydroxylapatite with either aqueous hydrochloric acid or with aqueous hydrochloric acid followed by aqueous magnesium chloride.

7. A composite which comprises a mixture of particulate ceramic hydroxylapatite and a polymerizable monomer or mixture of polymerizable monomers wherein said ceramic hydroxylapatite particles, prior to mixing with said polymerizable monomer or monomers, contain a first coat of a siliceous material selected from the group consisting of sodium silicate, sodium metasilicate and silicic acid and a second coat of an organosilane selected from the group consisting of γ-methacryloxypropyltrimethoxysilane and γ-methacryloxypropyl-tris-(β-methoxyethoxy) silane.

8. A composite according to claim 7 wherein said polymerizable monomers comprise a mixture of bis-GMA, 2,2-bis-propane dimethacrylate, and TEGMA, triethylene glycol dimethacrylate.

9. A composite according to claim 8 wherein said composite comprises 70 weight percent of ceramic hydroxylapatite and the balance a chemically-curable 7:3 mixture of said bis-GMA:TEGMA.

10. A composite according to claim 9 wherein said organosilane is γ-methacryloxypropyltrimethoxysilane.

11. A composite according to claim 10 wherein the particles of said ceramic hydroxylapatite have an average size of 5.3 μm.

12. A composite according to claim 11 wherein said ceramic hydroxylapatite particles are activated by etching, prior to silication, by stirring said hydroxylapatite with either aqueous hydrochloric acid or with aqueous hydrochloric acid followed by aqueous magnesium chloride.

13. A composite which comprises particulate ceramic hydroxylapatite coated with a siliceous material selected from the groyup consisting of sodium silicate, sodium metasilicate and silicic acid and embedded, after treatment with an organosilane selected from the group consisting of γ-methacryloxypropyltrimethoxysilane and γ-methacryloxypropyl-tris-(β-methoxethoxy)silane by adsorption or deposition of said organosilane from a solution thereof in an inert organic solvent, by polymerization within a mass of polymeric resin.

14. A composite according to claim 13 wherein said plymerized resin comprises a mixture of bis-GMA, 2,2-bis-propane dimethacrylate, and TEGMA, triethylene glycol dimethacrylate.

15. A composite according to claim 14 wherein said composite comprises 70 weight percent of ceramic hydroxylapatite and the balance a chemically cured 7:3 mixture of said bis-GMA:TEGMA.

16. A composite according to claim 15 wherein said organosilane is γ-methacryloxypropyltrimethoxysilane.

17. A composite according to claim 16 wherein said ceramic hydroxylapatite particles are activated by etching, prior to silication, by stirring said hydroxylapatite with either aqueous hydrochloric acid or with aqueous hydrochloric acid followed by aqueous magnesium chloride.

18. A composition adapted for use as a chemically cured dental restorative which comprises two pastes, (A) and (B), for admixture with one another prior to said dental restorative use, paste (A) comprising a mixture of particulate ceramic hydroxylapatite, a polymerizable monomer or mixture of polymerizable monomers and a catalyst for initiation of polymerization and paste (B) comprising a mixture of particulate ceramic hydroxylapatite, a polymeriable monomer or mixture of polymerizable monomers and a polymerization accelerator, wherein said particulate ceramic hydroxylapatite in each of said pastes contains a first coat of a siliceous material selected from the group consisting of sodium silicate, sodium metasilicate and silicic acid and a second coat of an organosilane selected from the group consisting of γ-methacryloxypropyltrimethoxy-silane and γ-methacryloxypropyl-tris-(β-methoxyethoxy) silane.

19. A composition according to claim 18 wherein said polymerizable monomers in each of said pastes (A) and (B) comprises a mixture of bis-GMA, 2,2-bis-propane dimethacrylate, and TEGMA, triethylene glycol dimethacrylate.

20. A composition according to claim 19 wherein each of said pastes (A) and (B) comprises 70 weight percent of said ceramic hydroxylapatite and the balance a 7:3 mixture of said bis-GMA:TEGMA.

21. A composition according to claim 20 wherein said organosilane is γ-methacryloxypropyltrimethoxysilane.

22. A composition according to claim 21 wherein paste (A) contains a 7:3:0.1 mixture of bis-GMA:TEGMA:BPO and paste (B) contains a 7:3:0.05 mixture of bis-GMA:TEGMA:DHET.

23. A composition according to claim 22 wherein said ceramic hydroxylapatite particles are activated by etching prior to silication by stirring said hydroxylapatite with either aqueous hydrochloric acid or aqueous magnesium chloride or with aqueous hydrochloric acid followed by aqueous magnesium chloride.

24. A composition adapted for use as an irradiation cured dental restorative which comprises a mixture of particulate ceramic hydroxylapatite, a polymerizable monomer or mixture of polymerizable monomers and a catalyst for initiation of polymerization by exposure to light, wherein said particulate ceramic hydroxylapatite contains a first coat of a siliceous material selected from the group consisting of sodium silicate, sodium metasilicate and silicic acid and a second coat of an organosilane selected from the group consisting of γ-methacryloxypropyltrimethoxy-silane and γ-methacryloxypropyl-tris-(β-methoxyethoxy) silane.

* * * * *